Figure 1:
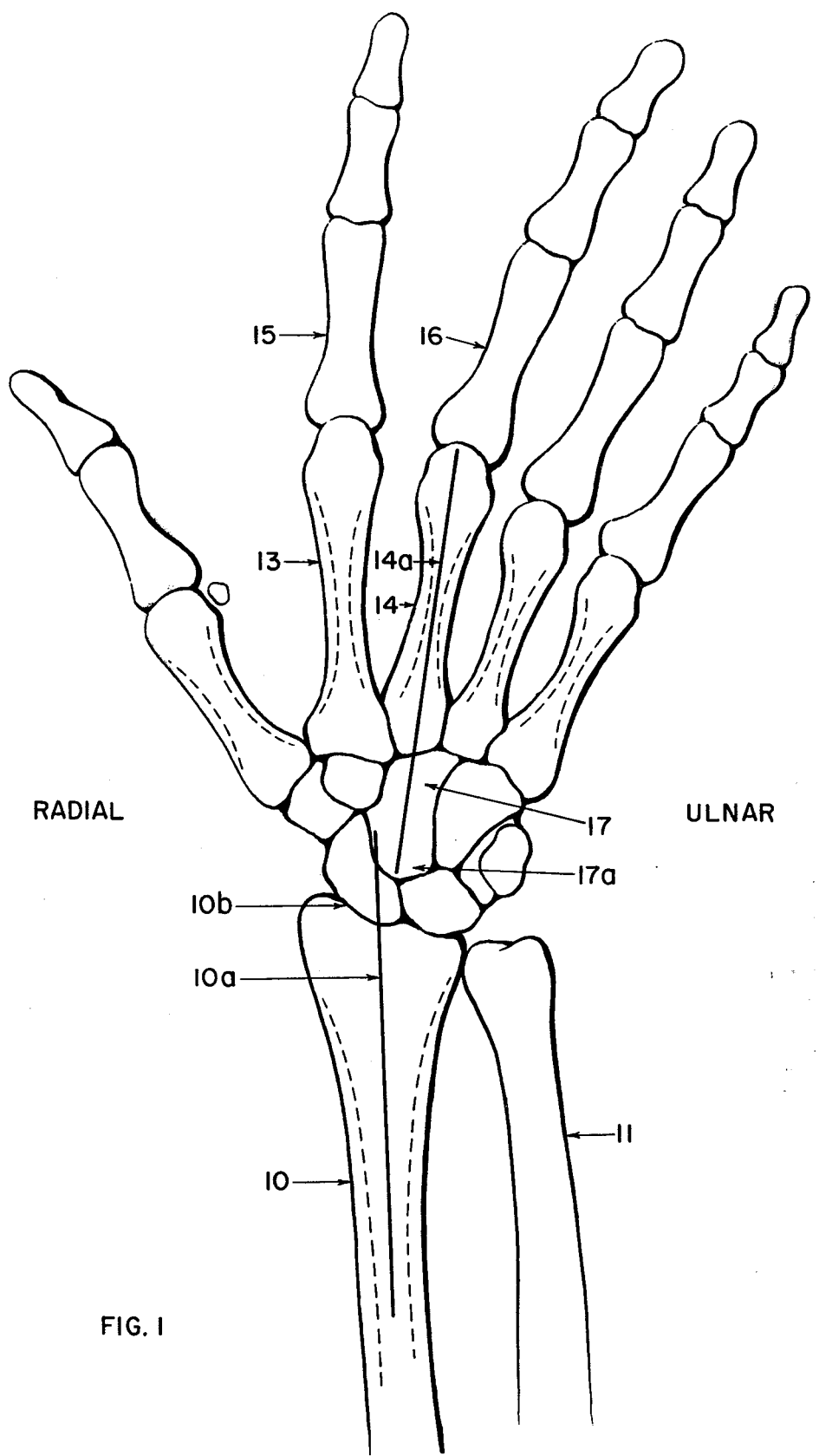

United States Patent [19]

Hamas

[11] 4,180,871
[45] Jan. 1, 1980

[54] PRE-CENTERED TOTAL WRIST PROSTHESIS

[76] Inventor: Robert S. Hamas, 2808 Beechwood Blvd., Pittsburgh, Pa. 15217

[21] Appl. No.: 847,841

[22] Filed: Nov. 2, 1977

[51] Int. Cl.² ............................................. A61F 1/24
[52] U.S. Cl. ...................................................... 3/1.91
[58] Field of Search ........................................... 3/1.91

[56] References Cited

U.S. PATENT DOCUMENTS

| 4,040,130 | 8/1977 | Laure | 3/1.91 |
| 4,063,314 | 12/1977 | Loda | 3/1.91 |
| 4,100,626 | 7/1978 | White | 3/1.91 |

OTHER PUBLICATIONS

Beckenbaugh et al., *Total Wrist Arthroplasty: A Preliminary Report*, The Journal of Hand Surgery, vol. 2, No. 5, pp. 337-344, Sep. 1977.
Volz, *The Development of a Total Wrist Arthroplasty*, Clinical Orthopaedics and Related Research, pp. 209-214, May 12, 1975.
Linscheid et al., *Total Arthroplasty of the Wrist to Relieve Pain and Increase Motion*, Geriatrics, pp. 48-52, Apr. 1, 1976.

*Primary Examiner*—Clifford D. Crowder
*Attorney, Agent, or Firm*—Webb, Burden, Robinson & Webb

[57] ABSTRACT

Total wrist prosthesis for restructuring a wrist which is diseased or damaged. The prosthesis is provided with four critical offsets to enable the axes of radial-ulnar deviation and flexion-extension motion of the restructured wrist to lie in planes offset from the axes of the third metacarpal and the distal radius, said planes including the axes of radial-ulnar deviation and flexion-extension motion of the normal wrist.

7 Claims, 6 Drawing Figures

PRE-CENTERED TOTAL WRIST PROSTHESIS

This invention relates to a mechanical device for surgical replacement of certain bones, joints, and associated ligaments in a diseased or otherwise damaged human wrist. More precisely, it relates to a prosthetic device that can be emplaced with a minimum of difficulty and with confidence that the restructured wrist will be properly balanced.

Generally speaking, the skeleton in the area of the wrist is composed of eight (8) irregularly shaped and arranged carpal bones which articulate with each other. Five (5) metacarpal bones extend proximally from the base of each finger and the thumb to articulate with the carpal bones. The capitate (one of the carpals) and the third metacarpal (proximal to the middle finger) move as a unit. The forearm skeleton is comprised of the radius which articulates with the carpal bones and the ulna around which the radius rotates at its distal end to rotate the forearm. The carpals between the distal end of the radius and the capitate move relative to both during wrist motion. Prior studies of healthy wrists have located the axis of radial-ulnar deviation of the wrist (thumb-side to little finger-side motion observed looking at the dorsum, i.e. back, of the wrist) to the ulnar-side of the axis of the third metacarpal and the axis of the distal radius within the head of the capitate bone. The axis of flexion-extension motion of the wrist (observed looking at the lateral aspect of the wrist) was known to be offset toward the palm (volarly) from the axes of the third metacarpal and distal radius and also located in the head of the capitate. In a normal wrist, the axes of deviation and motion do not intersect. The wrist is a biaxial joint with 2 degrees of freedom: flexion-extension motion and radial-ulnar deviation. The wrist does not rotate in relation to the radius; pronation and supination are due to rotation of the forearm.

Replacement of total wrists is a rather recent development. Nevertheless, a number of prosthetic devices are now available. These have been described in the literature, for example, Linscheid and Beckenbaugh "Total Arthroplasty of the Wrist to Relieve Pain and Increase Motion," *Geriatrics*, Apr. 1976 and "Total Wrist Arthroplasty: A Preliminary Report," *J Hand Surgery*, Sept. 1977, and Volz in *Clinical Orthopedics and Related Research*, May 1976. Prior total wrist prostheses all had a substantial drawback; namely, their designs as manufactured or as modified prior to or during the emplacing operation did not locate the axes of motion of the restructured wrists with the proper relationships to the axes of the third metacarpal and the distal radius. If the axes of motion are not located with the proper relationships to the axes of the third metacarpal and the distal radius the restructured wrist will not be balanced and the patient will not have proper function of the restructured wrist.

In many patients, disease has caused distortion of the wrist to such a degree that the individual carpal bones are almost unrecognizable grossly or on X-ray and the axes of motion of the diseased wrist no longer have their normal relationships to the axes of the third metacarpal and the distal radius. It has been the stated objective of surgeons to place the axes of motion of wrist prostheses through an area known as the head of the capitate if it were normally located—i.e., generally somewhere near where the axes of motion would be in the normal wrist. Because of the distortions caused by disease and since the head of the capitate along with some other carpal bones and the distal radius must be excised to allow space for the installation of the prosthesis, surgeons have not been able to precisely know or find where the axes of motion of the wrist prosthesis should be placed during the operative procedure. Some have attempted to bend and twist available devices at the operating table or just before to locate the axes of motion of the prosthesis so the wrist "feels" balanced. The process may involve the use of radiographs prior to and during the operation. This procedure has not been successful in placing the axes of motion of the prosthesis in their normal relationships to the axes of the third metacarpal and distal radius. Proper positioning of the axes of motion of the prosthesis is crucial to the success of the operation and in providing a restructured wrist which is balanced in regard to both flexion-extension and radial-ulnar deviation. If the axis of radial-ulnar deviation is placed too far radially, the ulnar deviators of the wrist have a mechanical advantage that tends to keep the hand tilted toward the ulnar side thus impairing function. If this axis of motion is placed too far ulnarly, the radial deviators of the wrist have a mechanical advantage that tends to keep the hand tilted toward the radial side. If the axis of flexion-extension motion is placed too far volarly (toward the palm), the extensors have the mechanical advantage causing excessive extension and limited flexion. If this axis of motion is placed too far dorsally (toward the back of the hand) the flexors of the wrist have a mechanical advantage so that a flexed position is predominant and extension is limited thereby impairing function.

It is an advantage according to this invention to provide a precentered total wrist prosthesis that can be easily emplaced in the shafts of the third metacarpal and the distal radius with the two critical axes in position for the best possible balancing and motion of the reconstructed wrist. The total wrist prosthesis is provided with critical offsets from radiographically observable reference axes.

Briefly according to this invention there is provided a total wrist prosthesis comprising a distal extension having an axis indentifiable from the radiographic profile for being aligned with the axis of the third metacarpal shaft when said distal extension is fixed to one or more metacarpals. The prosthesis has a proximal extension having an axis radiographically identifiable from the profile thereof for being aligned with the axis of the distal radial shaft and means for joining the distal and proximal extensions for biaxial or triaxial movement. The joint is arranged such that the axis for flexion-extension motion is volarly offset from the axis of the distal extension a distance "b" and from the axis of the proximal extension a distance "d." The axis for radial-ulnar deviation is ulnarly offset from the axis of the distal extension a distance "a" and from the axis of the proximal extension a distance "c." The ratios of the offset distances a, b, c, d to a common reference have the following ranges:

| Offset | Acceptable Range of Ratios | Preferable Ratios |
|---|---|---|
| a | .046–.058 | .052 |
| b | .13–.17 | .15 |
| c | .11–.13 | .12 |
| d | .08–.11 | .095 |

According to a preferred embodiment, the common reference is ninety-seven percent of the length of the patient's third metacarpal bone as observed on a posterior-anterior radiograph obtained by a standardized technique explained hereafter. It should be understood that the prosthesis according to this invention is not identical for left and right wrists. Looking at the posterior-anterior view of a prosthesis, the offsets "a" and "c" are in a different direction for left and right wrists (in each case that direction is ulnarly, however).

Figure 2:
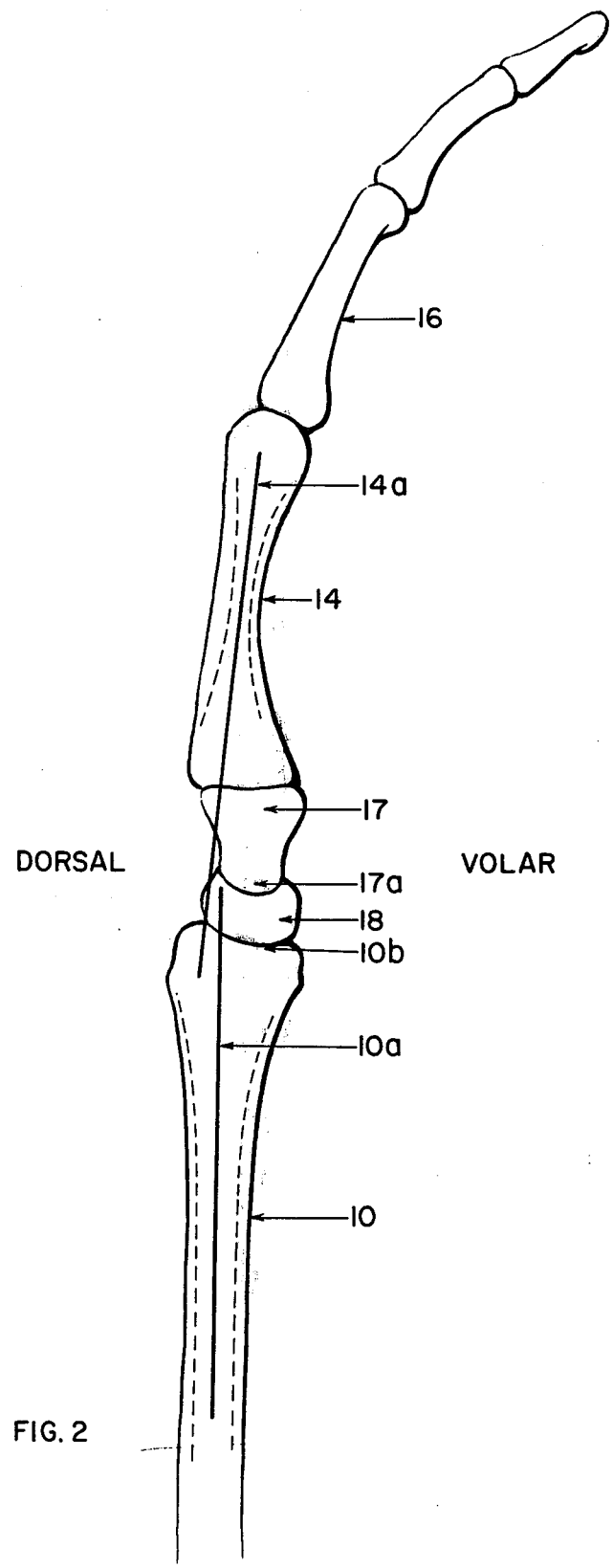
Figure 3:
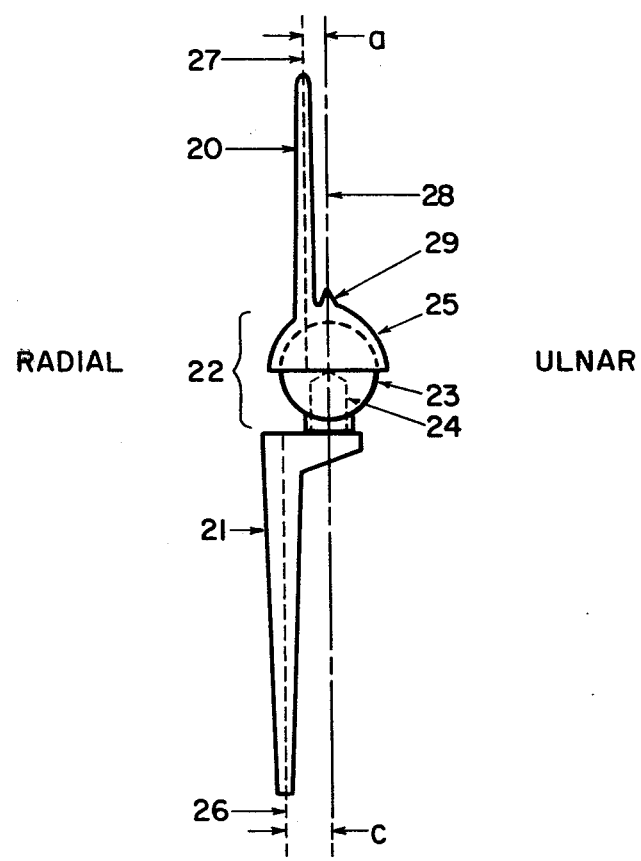
Figure 4:
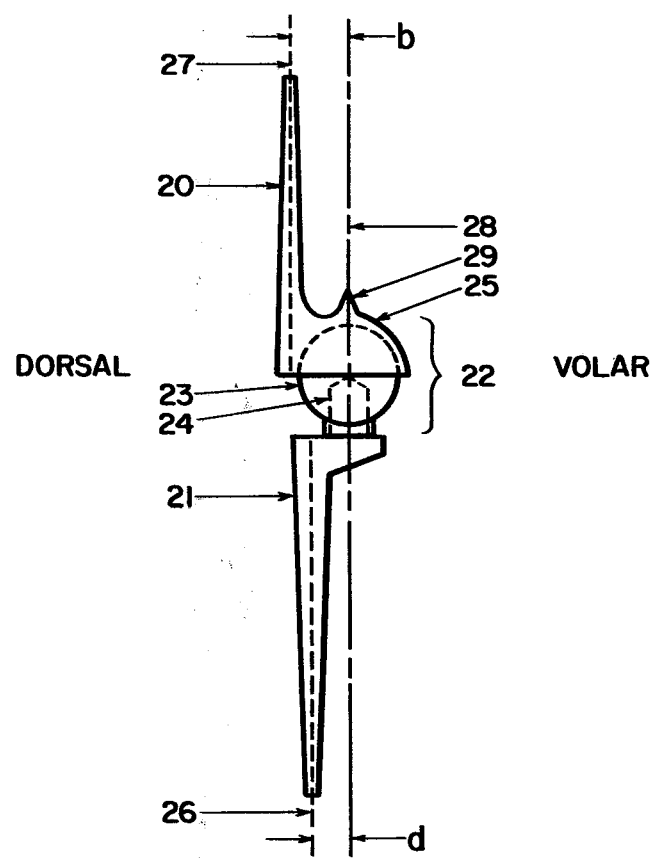
Figure 5:
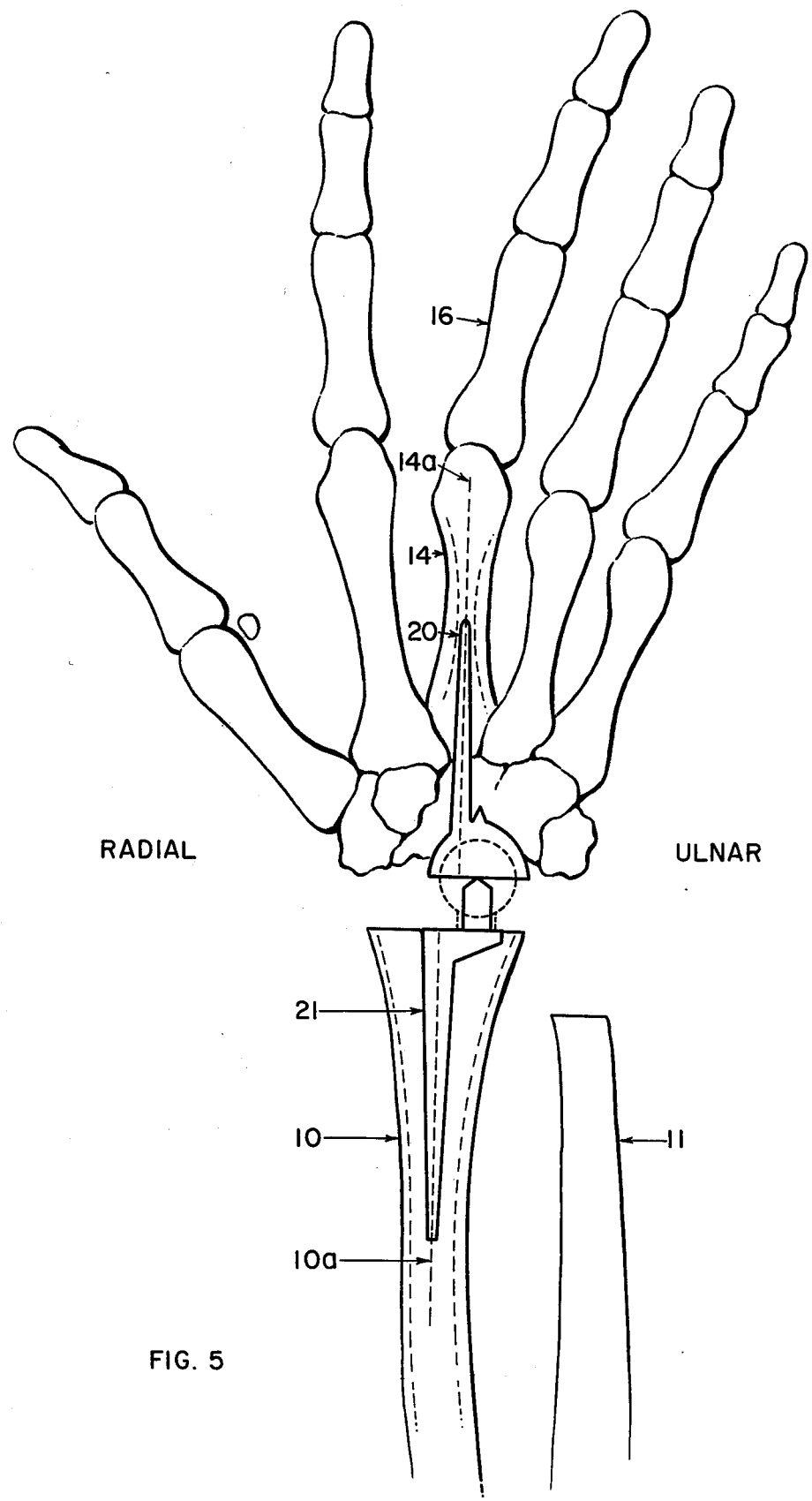
Figure 6:
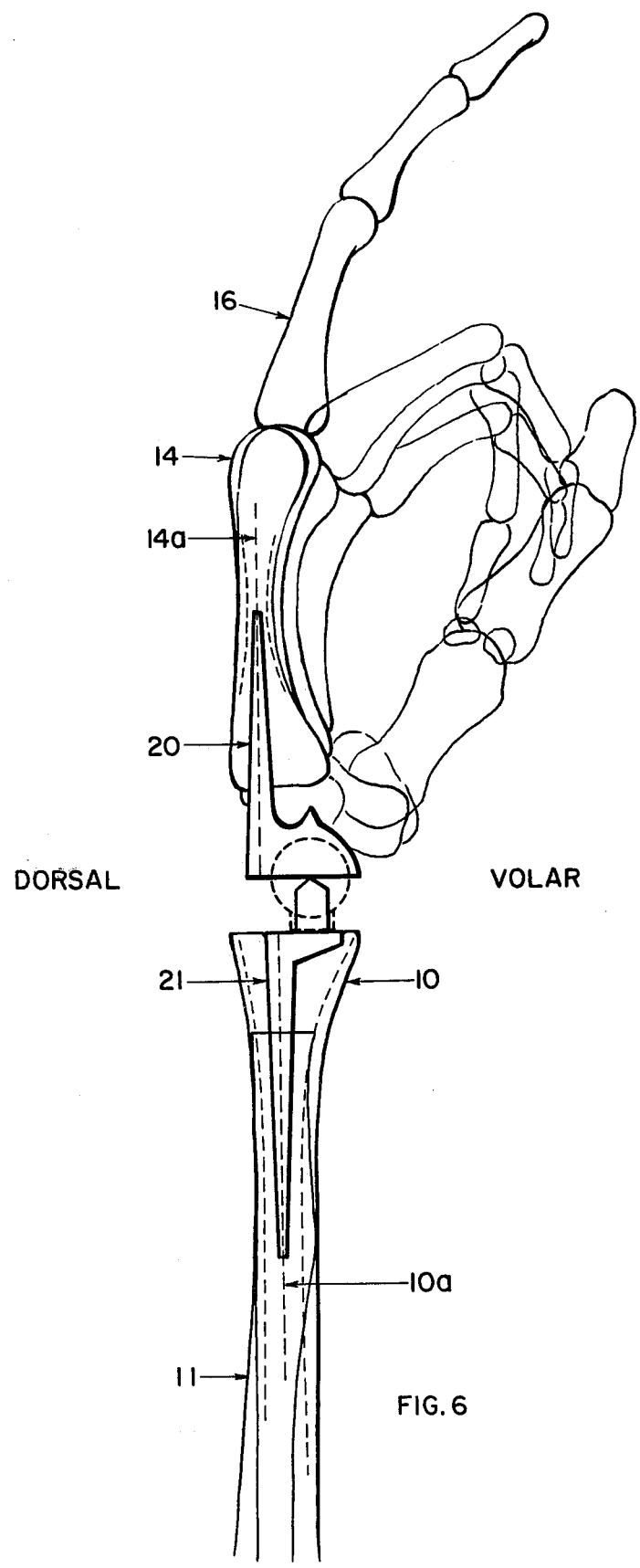

Further features and other objects and advantages of this invention will become clear from the following detailed description made with reference to the drawings, in which FIG. 1 is a schematic posterior-anterior view of the skeleton of a right wrist, FIG. 2 is a schematic lateral of the skeleton of a wrist observed with a number of bones omitted for simplicity, FIG. 3 is a schematic of a prosthetic device according to this invention illustrating key ulnar offsets for a right wrist, FIG. 4 is a schematic of a prosthetic device according to this invention illustrating key volar offsets, FIG. 5 is a posterior-anterior view similar to what would be observed by a standardized radiograph of a right hand having the total wrist prosthesis according to this invention properly installed, and FIG. 6 is a lateral view illustrating the appearance of a standardized radiograph of a hand having a total wrist prosthesis according to this invention properly installed.

Referring now to FIG. 1 there is shown in profile a healthy right wrist skeleton. The forearm is supported by two bones, the radius 10 and the ulna 11. They bear upon each other at their distal extremities and the distal face of the radius comprises an important articular surface 10b. FIG. 1 also illustrates the bones in the hand including the second metacarpal 13 and the third metacarpal 14 which are just behind the index 15 and middle finger 16 respectively. Eight carpal bones (the carpus) are shown between the articular surface 10b of the radius and the metacarpals. The capitate 17, a carpal behind the third metacarpal 14 is fixed relative to the third metacarpal. These two bones move as a unit to define the plane of the hand in both flexion-extension and radial-ulnar deviation.

The two axes of wrist motion were known to pass through an area known as the "head" 17a of the capitate 17. Two reference lines essential to an understanding of this invention are the axis of the distal radial shaft 10a (also referred to as the "distal radial axis") and the axis of the third metacarpal shaft 14a (also referred to as "the third metacarpal axis"). The critical axes and the length of the third metacarpal are located using radiographs employing the following standardized procedures. For the standardized posterior-anterior radiograph the arm is abducted ninety degrees and the elbow flexed ninety degrees. The palm is placed flat on the X-ray plate such that the second and third metacarpal heads touch the X-ray plate and the fingers are not rotated. The dorsum of the distal radius and ulna are placed in a plane parallel to the X-ray plate. The X-ray source is placed forty inches from the X-ray plate and the X-ray beam is centered on the wrist joint perpendicular to the X-ray plate. For the standardized lateral radiograph, the arm is adducted and the elbow flexed ninety degrees. The ulnar side of the forearm, hand and little finger are placed flat on the X-ray plate. In this view, the distal radius and ulna are superimposed. The dorsal cortex of the third metacarpal is positioned to be more dorsal than other metacarpal bones. The X-ray source is placed forty inches from the X-ray plate and the X-ray beam is centered on the wrist joint perpendicular to the X-ray plate.

The "axis of the distal radial shaft" is a line drawn through the shaft bisecting the medullary canal as viewed in radiographs taken as described in the preceding paragraph. The "shaft" is a straight portion of the radius for a distance of about fifty millimeters distal to the bowing of the mid-portion of the radius and proximal to the distal flaring of the radius. The "axis of the third metacarpal" is a line drawn through the third metacarpal bisecting the medullary canal as viewed in radiographs taken as described in the preceding paragraph. As used herein, the "length of the third metacarpal" is as measured only on the standardized posterior-anterior radiograph.

It should be appreciated that radiographs taken as explained above may result in a slight magnification of certain bones spaced above the plate. It has been found, however, that the length of the third metacarpal measured on the radiograph and physically measured (not possible on a patient's hand) are about the same due to a slight tilt relative to the plane of the metacarpal when the radiograph is being made by the standardized posterior-anterior technique. The dimensions of the prosthesis radiographically observed in the standardized views after being emplaced will be magnified about three percent.

From studies of normal adult hands using the standardized radiographs, applicant has found that the axis of radial-ulnar deviation is typically offset ulnarly from the third metacarpal axis a distance 0.052 times the length of the third metacarpal and is offset ulnarly from the axis of the distal radial shaft a distance being 0.12 times the length of the third metacarpal.

Referring now to FIG. 2 there is shown a lateral view of a partial skeleton of a healthy wrist viewed from the side thereof. The third metacarpal 14 and the capitate 17 are shown with the axis of the third metacarpal shaft 14a drawn thereon. These two bones move as a unit in flexion-extension motion. The radius 10 is illustrated with the articular surface 10b. Between the capitate 17 and the articular surface is the lunate 18 which rotates relative to both the radius and the capitate. From studies of normal adult hands, applicant has found that the axis of the flexion-extension motion is typically offset volarly from the third metacarpal axis a distance being 0.15 times the length of the third metacarpal and is offset volarly from the distal radial axis a distance 0.095 times the length of the third metacarpal. While there have been a number of studies of the kinematics of the human wrist and searches for the precise centers of the various motions of the wrist, it is applicant's belief that he was the first to find the axes of motion as defined by the above described offsets. These findings enable the emplacement of the following described total wrist prosthesis to precisely position the two critical axes in the restructed wrist in planes offset from the axes of the third metacarpal and distal radius, said planes including the axes of radial-ulnar deviation and flexion-extension motion in the normal wrist.

Referring now to FIG. 3, there is shown a posterior-anterior view of a right wrist prosthesis according to applicant's invention. The prosthesis has a distal extension 20 and a proximal extension 21 made from a corrosion resistant metal. Between the two extensions is a disengageable ball and socket joint 22. The sphere 23 is of a synthetic (for example, dense polystryene, polyethyene, etc.) material and is fixed to a post 24 connected to the proximal extension 21. The distal extension has a cup 25 with an inner spherical surface which rides over the ball. One can easily visualize the bisector 26 of the proximal extension 21. The bisector 26 is designed to be aligned with the axis of the distal radial shaft as defined previously. One can easily visualize the bisector 27 of the distal extension 20. The bisector 27 is designed to be aligned with the axis of the third metacarpal shaft. Hence, the bisectors are easily identifiable. A line through the axis of motion 28 for radial-ulnar deviation as seen in this posterior-anterior view of the joint permits observation of the ulnar offsets "a" and "c." Protuberance 29 is aligned with line 28 and provides an extra anchoring point for bone fixation since distal extension 20 is small to fit in the third metacarpal shaft.

FIG. 4 is very similar to FIG. 3 except that it is a lateral view of a wrist prosthetic device according to this invention. Like elements have like numeral designations. The bisector of the distal extension observable in the radiographic profile thereof is designed to be aligned with the axis of the third metacarpal shaft. The bisector of the proximal extension 21 is designed to be aligned with the axis of the distal radial shaft. These axes are observable radiographically. A line 28 through the axis of motion for flexion-extension motion of the joint parallel to the axes of the extensions is provided to enable the observation of the volar offsets "b" and "d."

Preferably the offsets a, b, c and d bear the following ratios to ninety-seven percent of the length of the patient's third metacarpal as seen on the standardized posterior-anterior X-ray: 0.052, 0.15, 0.12, and 0.095 respectively. It is permissible, however, if the ratios fall within the following ranges: 0.046–0.058; 0.13–0.17; 0.11–0.13; 0.08–0.11, respectively. This being the case three total wrist prostheses, sized as set forth in the following table will be useful for patients having metacarpal bones between about 51 and 74 millimeters on the standardized posterior-anterior radiograph (Each size must be provided in right and left design).

| | Length of 3rd Metacarpal | Offsets | | | |
| --- | --- | --- | --- | --- | --- |
| | | b | d | a | c |
| I | 51–57 | 7.9mm | 5.0mm | 2.7mm | 6.3mm |
| II | 57–66 | 9.0 | 5.7 | 3.1 | 7.2 |
| III | 66–74 | 10.3 | 6.5 | 3.6 | 8.2 |

The prosthesis must also have some indicia, preferably identifiable from the radiographic profile, to enable the surgeon to know at a glance that the correct angular orientation around an axis through the universal joint and parallel to the axes of the extensions has been achieved. This orientation is set when the wrist is open and the device observable. However, it is desirable to be able to check that the orientation is correct from the radiographs taken during the emplacing operation.

The length of the distal and proximal extensions from the center of motion of the universal joint for the devices shown in FIGS. 3 and 4 are 5 and 7 centimeters respectively. These are not critical dimensions. Clearly the extension must be long enough to be properly anchored in the particular shaft to which it is secured. Longer or shorter is not critical so long as the extension can be adequately fastened in place. The relative lengths of the distal and proximal extensions are not critical. For the device shown in FIGS. 3 and 4, the length of the distal extension is five-sevenths the length of the proximal extension.

The position of the center of motion of the universal joint relative to the proximal end of the third metacarpal is also not especially critical. This distance is usually determined by the amount of bones resected and extent of collapse of the wrist joint due to disease. To locate the axis of radial-ulnar deviation as it would be in a healthy wrist, the axis of motion of the joint should be approximately a distance one-quarter of the length of the third metacarpal proximal to the base of the third metacarpal. This position could also be defined from the articular surface of the distal radius. This is impractical since the distal radius is excised to remove deteriorated cartilage and bone and to provide room for placement of the prosthesis. It should be pointed out that if the offsets, a, b, c, and d are satisfactory, the center of motion of the joint (i.e., the intersection of the two axes of motion) will have a normal relationship to the axes of the third metacarpal and distal radius. Then the exact position proximal to the base of the third metacarpal is not critical and will not cause imbalance. This, of course, makes the surgeon's task somewhat easier. Nevertheless, the surgeon may desire to locate the axis of radial-ulnar deviation exactly the correct distance proximal to the base of the third metacarpal. For this reason, it is preferable according to this invention that the center of motion of the prosthesis be radiographically observable. This may be done by tapering the post 24 to a point at the center of motion. Since, the polystyrene ball is radiographically transparent, the tip is observable.

With the universal joint of the type shown in FIGS. 3 and 4 where the axes of radial-ulnar deviation and flexion-extension motion intersect, it is of course, impossible to place both axes in the location where they would be in a normal wrist as in the normal wrist the axes are offset. Providing the offset as in the normal wrist does not appear essential for good functioning of restructed wrists, but it should be understood that the applicant's invention is also applicable to prosthetic devices with nonintersecting axes. The universal joint should be disengageable but not necessarily so. While the extensions of the prosthesis are being inserted into position for cementing, they are not joined together. After the extensions are emplaced, the ball can be placed on the post 24 and the cup 25 eased into position over the ball.

Prostheses may be designed to restrict or permit rotation in relation to the radius. This invention has application to either type.

Prostheses may be designed without constraints or with constraints that limit the degree of rotation around the axis of radial-ulnar deviation and/or the axis of flexion-extension motion. The prostheses according to this invention should permit at least about 50 degrees radial-ulnar deviation and at least about 90 degrees of flexion-extension motion.

The prothesis shown in FIGS. 3 and 4 is made from rigid metallic or plastic (synthetic polymer) parts. It is possible that these parts be made from plastics that are not totally rigid in which event it may not be necessary to cement the extensions into the anchor holes described hereafter.

The techniques for installing the applicants prosthetic device are generally those used for installing prior devices. A tourniquet is applied to the upper arm. A dorsal incision is made from the distal radius toward the third metacarpal. Usual hand surgery procedures are used to expose the wrist joint including the carpus and the distal end of the radius. Bone resection now takes place to remove diseased and/or deteriorated bone and to provide space for the prosthetic wrist. The distal end of the radius is excised and typically the entire scaphoid and lunate are removed plus portions of the capitate, triquetrium, and hamate are removed. Holes are then drilled into the shafts of the distal radius and the third metacarpal into which the prosthetic device will be anchored. An attempt is made to drill the holes along the axes of the third metacarpal and distal radius. The prosthetic device is then trial fit and preferably radiographically examined to ascertain whether the axes of the prosthetic device align with the axes of the patient's third metacarpal and distal radius. In this case, a temporary metallic suture may be placed in the radius and/or remaining portion of the carpus to serve as a point of reference observable visibly and radiographically. Once the surgeon is satisfied with the position, the extensions of the prosthetic device are cemented in place.

Referring now to FIG. 5, there is shown the schematic of a radiograph of a wrist having the applicant's prosthetic device inserted therein. It is observable that the axes of the extension of the device are aligned with the reference axes of the patient's wrist as viewed posterior-anterior.

Referring now to FIG. 6, there is a lateral view of a patient's wrist wherein it can be seen that the axes of the prosthetic device are aligned with the critical axes in the patient's wrist.

FIG. 6 highlights a problem with aligning the distal device with the axis of the third metacarpal as viewed from the side. The various metacarpal bones are overlapped in this radiographic view. It is clear, however, that the dorsal edge of the third metacarpal is visible from the radiograph. The physcan may seek to position the axis of flexion-extension motion parallel to the dorsal cortex (outer edge) of the third metacarpal and offset volarly from the dorsal cortex approximately 0.2 (range about 0.17 to 0.23) times the length of the third metacarpal. This will typically place the axis of the distal extension of the prosthetic device along the axis of the third metacarpal shaft.

It is not of course always possible to perfectly align the axes of the extensions of the prosthetic device with the axes of the patient's third metacarpal and distal radius; however, if the alignment is within a millimeter, satisfactory results (a balanced wrist) will be achieved. This degree of precision is obtainable.

Having thus described my invention with the detail and particularity required by the Patent Laws, what is desired protected by Letters Patent is set forth in the following claims.

I claim:

1. A total wrist prosthesis comprising a distal extension having a longitudinal axis identifiable from the profile thereof for being aligned with the longitudinal axis of the third metacarpal when the said distal extension is fixed to one or more metacarpals, a proximal extension having a longitudinal axis identifiable from the profile thereof for being aligned with the longitudinal axis of the distal radius and means for joining the distal and proximal extensions for biaxial or triaxial movement, the axis for flexion-extension motion volarly offset from the axis of the distal extension a distance "b" and from the axis of the proximal extension a distance "d," the axis for radial-ulnar deviation being ulnarly offset from the axis of the distal extension a distance "a" and from the axis of the proximal extension a distance "c," wherein the ratios of a, b, c and d to a common reference are 0.046–0.058, 0.13–0.17, 0.11–0.13, and 0.08–0.11, respectively said common reference being a length between about 51 and 74 mm.

2. The total wrist prosthesis according to claim 1 wherein the ratios of a, b, c and d to a common reference element are about 0.052, 0.15, 0.12, 0.095 respectively.

3. The total wrist prosthesis according to claim 1 wherein the axes for radial-ulnar deviation and for flexion-extension movement intersect.

4. The total wrist prosthesis according to claim 1 wherein the means for joining is a ball and socket joint.

5. The total wrist prosthesis according to claim 1 wherein the axis of radial-ulnar deviation and the axis of flexion-extension motion are radiographically observable.

6. The total wrist prosthesis according to claim 1 wherein the angular position around an axis generally parallel to the axes of the extensions is radiographically observable.

7. The total wrist prosthesis according to claim 1 wherein the common reference is ninety-seven percent of the length of the third metacarpal as viewed in the standardized posterior-anterior radiograph.

* * * * *